(12) United States Patent
Halalay et al.

(10) Patent No.: US 7,362,110 B2
(45) Date of Patent: Apr. 22, 2008

(54) MEASUREMENT CELL FOR LIQUIDS

(75) Inventors: Ion C. Halalay, Grosse Pointe, MI (US); R. Vance Mc Cabe, Jr., Fenton, MI (US)

(73) Assignee: GM Global Technology Operations, Inc., Detroit, MI (US)

( * ) Notice: Subject to any disclaimer, the term of this patent is extended or adjusted under 35 U.S.C. 154(b) by 385 days.

(21) Appl. No.: 11/100,015

(22) Filed: Apr. 6, 2005

(65) Prior Publication Data

US 2006/0226859 A1 Oct. 12, 2006

(51) Int. Cl.
*G01R 27/08* (2006.01)
*G01N 33/26* (2006.01)

(52) U.S. Cl. .................. 324/698; 324/693; 340/631

(58) Field of Classification Search ............... 324/698, 324/442; 340/631
See application file for complete search history.

(56) References Cited

U.S. PATENT DOCUMENTS

| | | | |
|---|---|---|---|
| 3,422,417 A * | 1/1969 | Lowe ........................ | 340/631 |
| 5,402,113 A * | 3/1995 | Naas ........................ | 340/631 |
| 5,457,396 A * | 10/1995 | Mori et al. ................. | 324/724 |
| 5,523,692 A * | 6/1996 | Kuroyanagi et al. ........ | 324/438 |
| 5,852,404 A * | 12/1998 | Amini ....................... | 340/627 |
| 6,774,645 B1* | 8/2004 | Leidl et al. ................. | 324/698 |
| 6,822,461 B2* | 11/2004 | Klun ......................... | 324/698 |
| 6,861,851 B2* | 3/2005 | Lvovich et al. ............. | 324/698 |

OTHER PUBLICATIONS

Zeitschrift fur Instrumentenkunde, vol. 53, Issue 1, Jan. 1933 (German language document, Applicants' English translation enclosed).

\* cited by examiner

*Primary Examiner*—Andrew H. Hirshfeld
*Assistant Examiner*—John Zhu

(57) ABSTRACT

A cell for the measurement of resistivity and/or permittivity of a liquid, under variable ac frequency energizing, preferably includes a first set of n+1 metal plates interleaved with a second set of n places, both sets of plates preferably being of the same size and shape for the liquid filling the spaces between facing plates. The two sets of alternating plates are separately electrically interconnected. The plates are supported at their peripheries in spaced apart and insulated relationship so that, during variable ac frequency testing, current flow through the liquid is in a path perpendicular to the facing plates.

12 Claims, 3 Drawing Sheets

MEASUREMENT CELL FOR LIQUIDS

TECHNICAL FIELD

This invention pertains to a device for ac impedance measurements on fluids, especially liquids. More specifically this invention pertains to an ac measurement cell for determining electrical properties (resistivity and permittivity) of liquids such as lubricating oils in working mechanisms such as automobile engines.

BACKGROUND OF THE INVENTION

There is a need to determine the properties of fluids in a working environment. For example, it would be advantageous to be able to measure certain electrical properties of lubrication oils circulated in operating machines and engines as a basis for determining the remaining useful life of the fluid. Hydrogen-containing and carbon- and/or silicon-containing lubricants are often used in mechanisms and the lubricants are often heated in their working environments to temperatures in excess of 100° C. Such measurements require a fixture comprising a measurement cell and an enclosure through which a representative stream of the oil is circulated from time to time during its working life. The sensor must be capable of fast and accurate determinations of electrical properties of the fluids over an extended time without being degraded by the material.

SUMMARY OF THE INVENTION

A durable, simple and effective capacitance and resistance measuring device is provided that can be filled with a fluid under test in order to determine its ac electrical properties. The measuring device can operate in the batch mode by filling the device with liquid and closing it, or in the flow-through mode with the liquid under test flowing through it. The measurement device (or cell) is connected to suitable impedance measuring instrumentation and its electrical impedance is determined over some frequency range of interest. The electrical resistivity of the fluid can then be determined from the measured resistance and the cell constant, and the electrical permittivity of the fluid can be determined from the measured capacitance and the vacuum capacitance of the cell.

The measurement cell includes a first set of electrically conductive metal plates interleaved in parallel and equally spaced facing relationship with a second set of conductive metal plates. In a preferred embodiment, the first set has n+1 plates and the second set has n plates (where n is an integer and has a value of 1 or more). Thus, in the preferred embodiment, the top and bottom plates of the interleaved stack are plates of the first set. The size, number (preferably 2n+1), spacing, and construction material of the plates is usually determined by the conductivity and nature of the liquid whose properties are to be measured. For most measurement applications the thickness of the plates is suitably in the range of about 0.1 mm to about 2 mm. It is generally preferred that the facing surfaces of the plates of the two sets are of the same size and shape. Round plates or plates with a regular polygonal shape are particularly useful.

Each pair of the first set of plates are electrically connected by a first set of connectors which are suitably insulated to avoid any electrical connection with an intervening plate of the second set of plates. Similarly, the plates of the second set are electrically connected by a second set of like insulated connectors. In a preferred embodiment of the measurement cell assembly, each interposed plate has holes at its periphery for pass-through of inserted, insulated conductors connecting overlying/underlying plates of the other set. But, obviously, many other interleaved plate designs are available for connecting sandwiching pairs of plates without electrically contacting the interposed plate. The architecture of the assembled plates and insulating layer on the exterior surface of each connector body ensures that the electric field lines, and thus the electric current flow in the cell, are perpendicular to each pair of facing plates.

The stack of interposed sets of plates is supported in a suitable housing member but insulated from electrical contact with the housing. In a preferred embodiment with insulated tubular connectors, the stack is mounted rigidly to a cell mounting flange by rigid plastic bolts through holes in the periphery of the plates and the connector tubes. The bottom plate is suitably insulated from the mounting flange. A housing cover fitted and sealed against the mounting flange encloses the stack. Liquid for testing can be introduced into and removed from the measurement fixture by means of two fluid ports in the housing. Both cell housing members are made of metal and connected to electrical ground. The housing members effect electrical shielding of the stack of plates and connectors constituting the measurement fixture.

Electrical connections between the measurement cell and measuring electronics are suitably provided by two or, preferably, four coaxial cables through a sealed cable port in one of the housing members. The two cables are connected to a selected plate from each set of plates. If four cables are used, then the cables are connected pair wise to the selected plates.

The cell is capable of measuring the properties of highly conductive fluids, such as electrolyte solutions, as well as highly resistive liquids, such as engine oils, by adjusting the number of plates, their dimensions and/or the inter-plate spacing. The measurement accuracy of a preferred embodiment of the device has been determined to be at least ±0.2%. The cell is suitable for electrical ac impedance measurements up to a frequency of 100 MHz.

Other objects and advantages of the invention will be apparent from a detailed description of specific embodiments of the measurement cell which follows.

DESCRIPTION OF PREFERRED EMBODIMENTS

The electrical conductivity κ and the electrical resistivity ρ of a material are physical quantities that are inversely related; they are reciprocals of each other. Thus, a measurement of either conductivity or resistivity is essentially a determination of the other. This specification will refer to measurements of resistivity (as well as permittivity) with the intention that the term "resistivity" in that context includes "conductivity."

A first embodiment of the invention is a measurement cell for a fully formulated commercial hydrocarbon based lubricating oil in an operating hydrocarbon fueled internal combustion engine. Such petroleum oils, produced as refined distillation products of crude petroleum, generally range from low viscosity, with molecular weights as low as 250, to very viscous lubricants, with molecular weights up to about 1000. The physical properties and performance characteristics of such engine lubricants depend on the relative distribution of parafinic, aromatic, and alicyclic (naphthenic) components. Depending upon the engine application, these refined oils are formulated to contain special additives such as oxidation inhibitors, rust inhibitors, anti-wear and extreme pressure agents, friction modifiers, detergents, pour-point depressants, viscosity-index improvers, foam inhibitors, and dispersants for contaminants.

In a representative automobile engine, a petroleum oil (mineral-based) is pumped from a sump in the crankcase and sprayed and circulated around and over rotating and reciprocating members of the engine. The oil is heated by the engine to temperatures in the range of, for example, about 50° C. to about 150° C. and exposed to an oxidizing atmosphere. From time to time, during engine operation, a small representative portion of the circulating oil is diverted through a suitable compact impedance sensor located conveniently in oil passages, the oil pan, or any other suitable location on or near the engine. The sensor is arranged and constructed to permit oil to flow through it in one or more relatively thin film streams for determination of the present-time resistivity of the fluid. A record (history) of resistivity ρ values of the working oil are obtained during operation of the engine. Permittivity ε values are readily obtained at the same time and may also be used in predicting remaining oil life. FIGS. 1-10 of this specification illustrate a measurement cell suitable for such high resistivity liquids.

Figure 1:
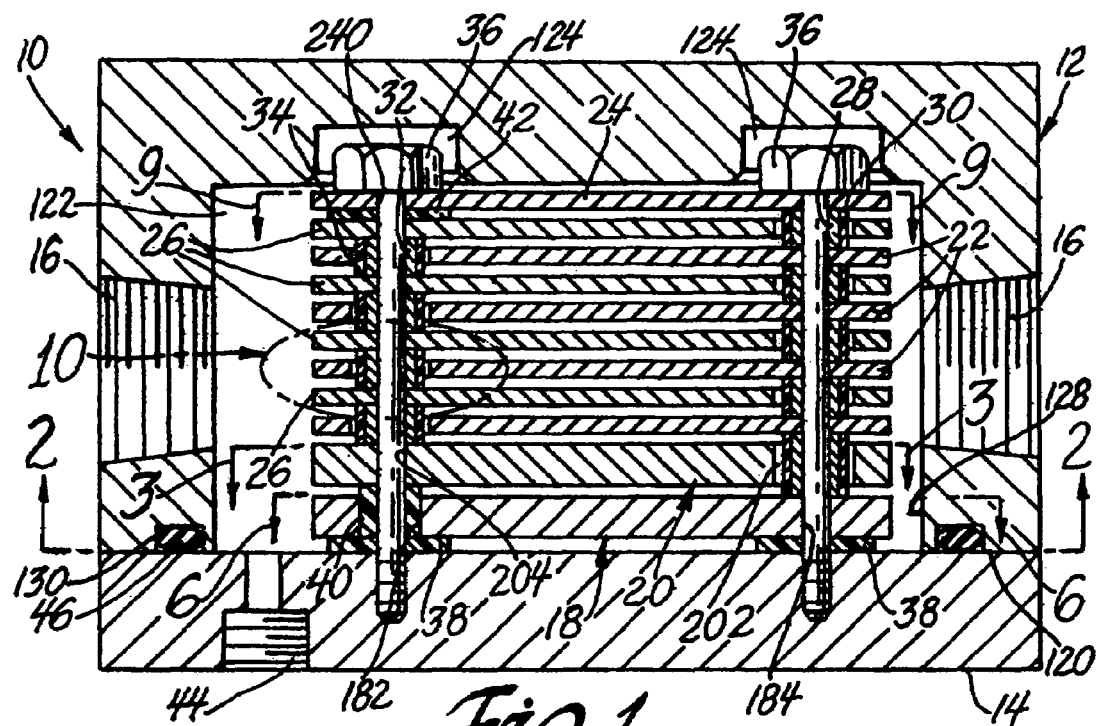
FIG. 1 is an elevational view in cross-section of an embodiment of a measurement cell of this invention.

FIG. 1 illustrates a cross-section of a measurement cell 10. Measurement cell 10 comprises a cell housing 12 and a cell mounting flange 14. Cell housing 12 has opposed fluid ports 16 permitting engine oil to enter, flow-through, and exit the measurement fixture. In applications where the properties of the liquid are not to be measured under flowing conditions, the liquid is added to the cell housing 12 to fill it and the ports 16 closed to retain the liquid until the electrical measurements are completed. Cell housing 12 and cell mounting flange are suitably made of aluminum alloy.

Within cell housing 12 is a stack of a first set of six plates interleaved or interposed with a second set of five plates. The first set of plates includes a connector plate 18 which is the current-gathering plate for a first set and is located at the bottom of the stack near cell mounting flange 14. The first set of plates also includes four intermediate plates 22 and top plate 24. The second set of plates includes a lower current-collecting, connector plate 20 and four upper plates 26. In this embodiment, the plates are round (about 45 mm in diameter) and made of stainless steel for durability in the hot oxidizing engine oil environment. The connector plates 18, 20 to which co-axial cable connections are made as described below, are suitably about 3 mm thick while the other plates are suitably about 1.5 mm thick. Each plate is spaced about one millimeter from a facing neighboring plate of the other set of plates.

Three groups of five, vertically oriented, round stainless steel connector tubes 28 (one group shown in the sectional view of FIG. 1) support the first set of plates 22, 24 over connector plate 18. Each connector tube 28 has an electrically insulating layer 30 (suitably Teflon) on its outer cylindrical surface. The purpose of insulating layers 30 is to electrically isolate the connectors 28 for the first set of plates from the interposed members of the second set of plates 20, 26. The vertical columns of connector tubes 28 are arcuately spaced at angles of 120° about the periphery of the plates. Similarly, three groups of four, vertically oriented, round stainless steel connector tubes 32 support the second set of plates 26 over connector plate 20. The outer cylindrical surfaces of connector tubes 32 are also covered with Teflon insulating layers 34 to electrically isolate connectors 32 for the second set of plates from circular edges of interposed members of the first set of plates. The vertical columns of connector tubes 32 are arcuately spaced 120° from each other between columns of connector tubes 28 and spaced 60° from the columns of tubes 28.

The vertical stack of interposed first and second sets of plates are securely attached to cell mounting flange 14 by six rigid, electrically non-conducting plastic bolts 36 (two bolts 36 are visible in the diametric sectional view of FIG. 1) spaced at 60°. The bolts pass through the six groups of hollow connector tubes 28, 32. The heads of the bolts 36 engage and compress against the top surface of top plate 24 (of the first set of plates). Six insulating washers or spacers 38 around the lower ends of bolts 36 (two shown in FIG. 1) electrically insulate the bottom surface of bottom collector plate 18 from cell mounting flange 14. Three electrically insulating bushings 40 (one shown in FIG. 1) arcuately spaced at 120°, space and support connector plate 20 (second set) above connector plate 18 (first set). And three insulating washers 42 (one visible in FIG. 1) arcuately spaced at 120°, separate and insulate top plate 24 (first set) from the adjoining plate 26 of the interposed second set.

Electrical connections between the measurement cell 10 and measuring electronics are suitably provided by two or, preferably, four coaxial cables, not shown, through a threaded cable port 44 in cell mounting flange 14. The two cables are connected, respectively, to connector plates 18 and 20. If four cables are used, then the cables are connected pair wise to the selected plates. Suitable terminal ends from the cables are inserted into terminal receptacle holes as will be described with respect to FIGS. 3, 5, 6, and 8. If necessary, epoxy sealant or the like is used to seal the cable port 44 from the environment. Cell housing 12 is sealed against cell mounting flange by o-ring 46. Mounting flange 14 is fastened onto the cell housing 12 by means of four threaded bolts (not shown) suitably placed near the outside circumference of o-ring 46. Cell housing 12 and mounting flange are electrically grounded and provide shielding for the two sets of plate stacks.

Figure 2:
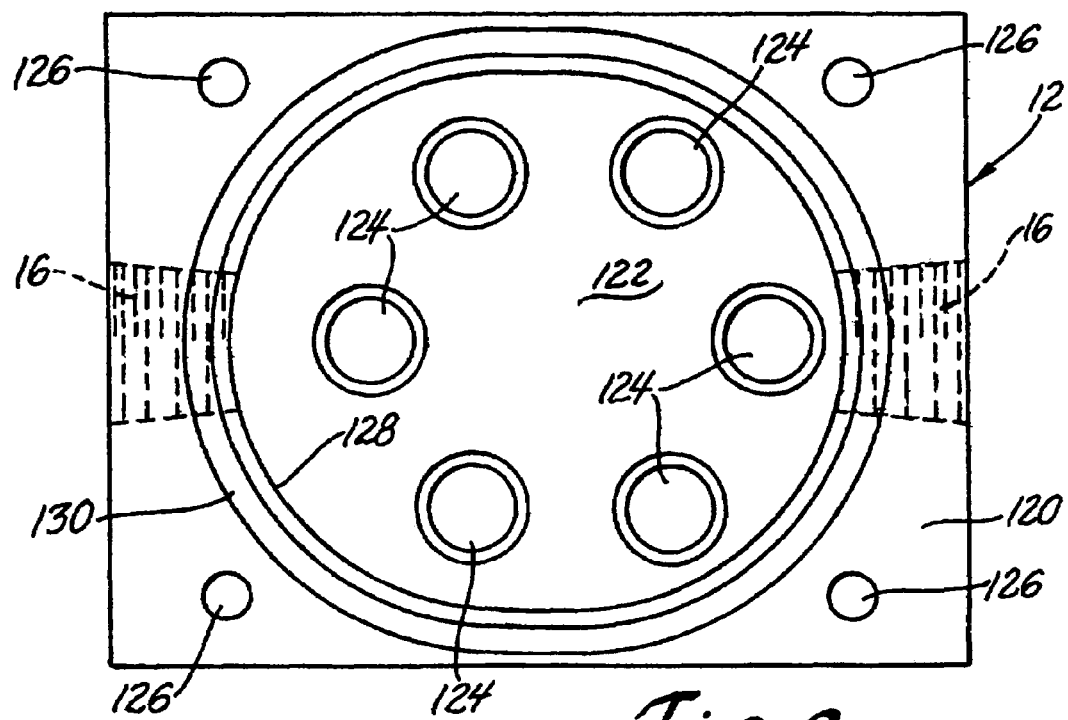
FIG. 2 is an interior view of the inside of the cell housing of FIG. 1 as viewed in location and direction 2-2 indicated in FIG. 1.

As indicated by directional arrows 2-2 in FIG. 1, FIG. 2 is a view looking into the interior of an empty cell housing 12 before it has been placed over a stack of interposed first and second sets of plates. Cell housing 12 has a flat bottom surface 120 for sealing engagement with upper surface of cell mounting flange 14. Cell housing 12 also has a vertical interior side wall 128 sized and shape to enclose the plate stacks. The top interior surface 122 of housing 12 has six arcuately spaced bores 124 for receiving the heads of plastic bolts 36 and oval shaped groove 130 machined into bottom surface 120 receives o-ring 46 (FIG. 1). Bolt holes 126 are provided in cell housing 12 for securely attaching (bolts not shown) the housing 12 to cell mounting flange 14 (threaded bold holes not illustrated).

Figure 3:
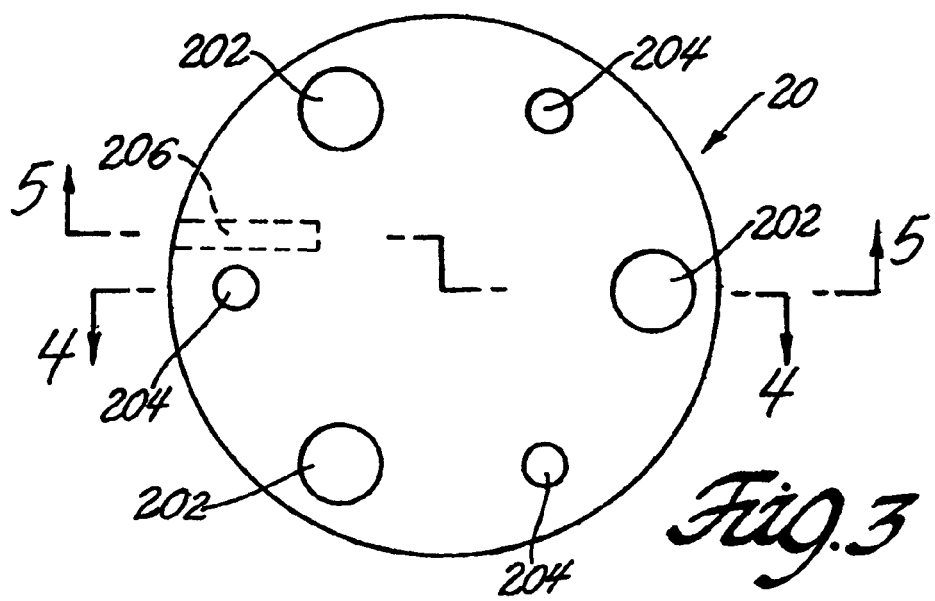
FIG. 3 is a plan view of a connector plate (second set) as viewed in the location and direction 3-3 indicated in FIG. 1.
Figure 4:
FIG. 4 is a first sectional view of the connector plate shown in FIG. 3 taken at the location and direction 4-4 indicated in FIG. 3.
Figure 5:
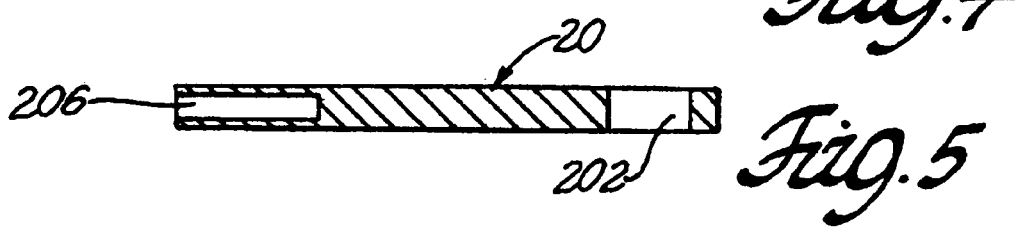
FIG. 5 is a second sectional view of the connector plate shown in FIG. 3 taken at the location and direction 5-5 indicated in FIG. 3.

FIG. 3 is a plan view (in direction 3-3 of FIG. 1) of circular connecting plate 20 for the second set of plates. FIGS. 4 and 5 are sectional views of connector plate 20 taken at positions 4-4 and 5-5 and in the directions indicated in FIG. 3. Connecting plate 20 has holes centered on a circular center line just inside the outer edge of plate 20 and spaced at 60° angles. Larger holes 202 receive three connectors 28 with their insulated coating layers 30 (for the first set of plates). Bolts 36 pass through the smaller holes 204. Round slot 206 (FIGS. 3 and 5) is formed inwardly from the circumferential edge of plate 20 to receive a terminal end of connector of a coaxial cable.

Figure 6:
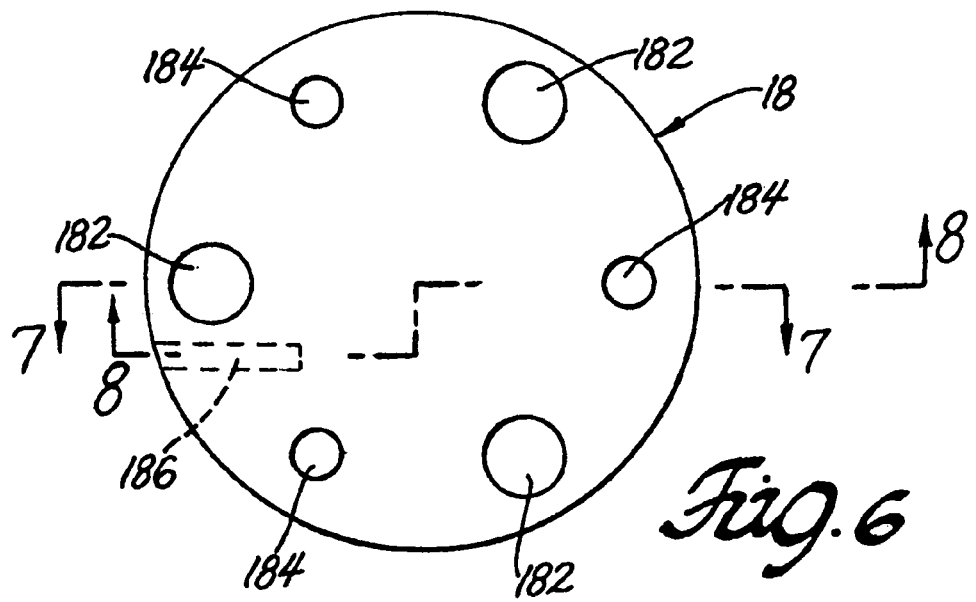
FIG. 6 is a plan view of a connector plate (first set) as viewed in the location and direction 6-6 indicated in FIG. 1.
Figure 7:
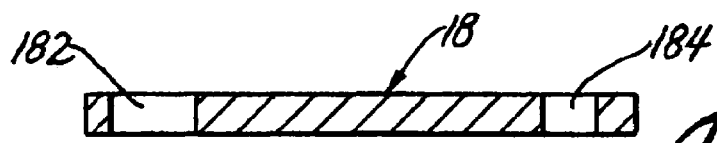
FIG. 7 is a first sectional view of the connector plate shown in FIG. 6 taken at the location and direction 7-7 indicated in FIG. 6.
Figure 8:
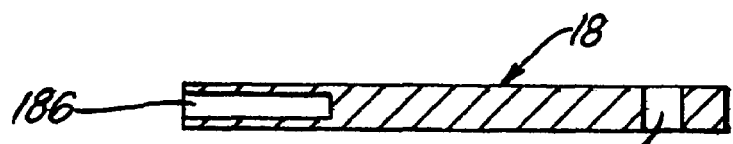
FIG. 8 is a second sectional view of the connector plate shown in FIG. 6 taken at the location and direction 8-8 indicated in FIG. 6.

FIG. 6 is a plan view (in direction 6-6 of FIG. 1) of circular connecting plate 18 for the first set of plates. FIGS. 7 and 8 are sectional views of plate 18 taken at positions 7-7 and 8-8 and in the directions indicated in FIG. 6. Like connecting plate 20, connecting plate 18 has holes spaced at 60° angles on a circular center line just inside its outer edge. Larger holes 182 receive three connectors 28 with their insulated coating layers 30 (for the second set of plates). However, large holes 182 are located in a vertical line with the small holes 204 in plate 20. Bolts 36 pass through the smaller holes 184. Round slot 186 is formed inwardly from the circumferential edge of plate 18 to receive a terminal end of connector of a coaxial cable. Slot 186 is offset from slot 206 in plate 20 to facilitate insertion of coaxial cable terminals in the stacked connector plates 18 and 20.

Figure 9:
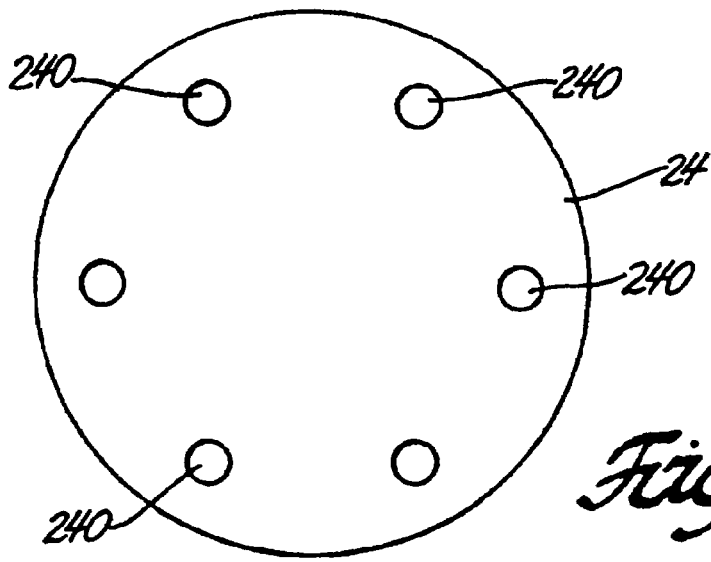
FIG. 9 is a plan view of the top plate (first set) taken at the location and direction 9-9 of FIG. 1.

FIG. 9 is a plan view (in direction 9-9 of FIG. 1) of top plate 24 (set one). Top plate 24 is an end plate of the stack and requires only the relatively small bolt holes 240.

Figure 10:
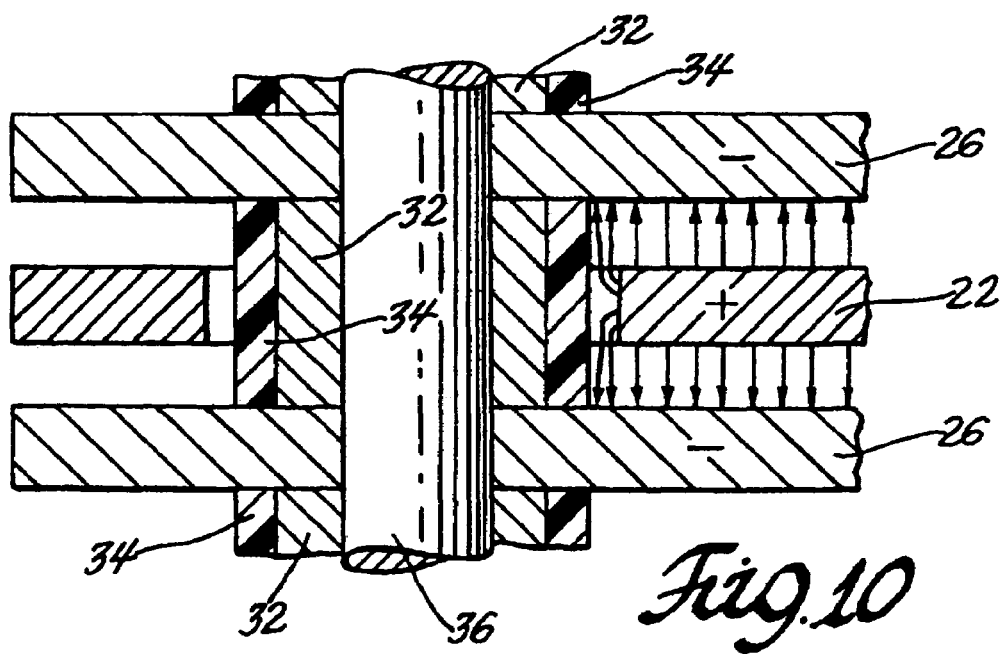
FIG. 10 is an enlarged view of circled portion 10 of FIG. 1.

FIG. 10 is an enlarged view of the plate stack portion of FIG. 1 at location 10 indicated in FIG. 1. The measurement cell 10 normally is activated by a very high frequency alternating current potential. In FIG. 10 the polarity of the plates is illustrated at an arbitrary moment in time for a very small fraction of a second. In this exemplary illustration plate 22 (first set) is electrically positive and facing plates 26 (second set) are electrically negative. Plates 26 are physically separated by metal electrical connector tubes 32 with their outer insulator layers 34. The circular edge of plate 22 may lie close to insulator layer 34. Still, the instantaneous current flow from plate 22 to both facing plates 26 is perpendicular to plates 26. When the current flow is reversed the same current path is obtained in the opposite but perpendicular direction. This is necessary to the intended function of the cell and a benefit of the use of electrical insulation, such as layers 30, 34 on tubular connectors 28, 32, at the edges of the interposed plates.

Thus, the cell design embodiment illustrated in FIGS. 1-10 achieves the desired high frequency alternating current flow in a perpendicular path between an interposed plate and facing plates. However, obviously, many other cell construction embodiments achieve the same result. For example, in an alternative embodiment, the plates of the cell can be separated by slots in a supporting insulating material, while the electrical contact between the plates of each set is made on their edges with a layer of electrically conductive material existing inside each slot. The conductive layers of alternate slots are in contact with each other. The conductive layers may be made of pieces of an electrically conductive sheet, or may be deposited by physical or chemical means at selected places within the slots. Alternatively, the electrical contact between the plates of each set may be made through wires connected to each plate of the set.

When data concerning the properties of the oil are required, the sensor is powered by a suitable AC frequency generator. The input voltage to the sensor creates a time-varying electric field inside the fluid under test. The output current and phase angle between the output current and applied voltage are sensed and this data, together with the value of the input voltage, is directed to a local microprocessor, which in automotive applications may be the engine's control module. The voltage, current and phase-angle signals are then used to calculate the impedance amplitude, the resistance and the reactance of the sensor-oil combination, and these values are used in turn for determining the electrical resistivity (or conductivity) and, optionally, additionally the permittivity of the oil passing through the sensor. The oil property data (resistivity $\rho$ and permittivity $\epsilon$) is stored in the on-vehicle (or on-engine or on-machine) microprocessor for subsequent processing and analysis. The oil temperature is also recorded at the time when the electrical property data is obtained.

The measurement cell of this invention has been illustrated by an illustrative embodiment. But, obviously, other forms of the sensor with current flow directed perpendicularly between facing plates could readily be adapted by one skilled in the art. The invention is not to be limited by the illustrated embodiment.

The invention claimed is:

1. A measurement cell for determining the resistivity and/or permittivity of a liquid, the cell comprising:

a first and second set of electrically conductive metal plates with each plate having opposing plate faces, the first set of plates being interleaved in parallel and equally spaced plate facing relationship with the plate faces of the second set of electrically conductive metal plates, the number of plates respectively in the first set and second set, the dimensions of the plates, and the spacing between the alternating plates of the first and second sets being predetermined for the liquid to be placed or flowed between them for determination of the present value of the liquid's resistivity and/or permittivity;

a first set of electrical connectors between pairs of plates of the first set, the first set of electrical connectors being electrically insulated with a first insulation layer from interposed plates of the second set of plates;

a second set of electrical connectors between pairs of plates of the second set, the second set of electrical connectors being electrically insulated with a second insulation layer from interposed plates of the first set of plates; and a first electrical connection to one plate of the first set of plates and a second electrical connection to one plate of the second set of plates for delivery of variable and high frequency electrical signals to the plates; the insulation of the first and second sets of electrical connectors between facing plates promoting current flow through an intervening liquid perpendicularly to the faces of each pair of facing plates.

2. A measurement cell as recited in claim 1 in which the first set of electrically conductive metal plates has one more plate than the second set of electrically conductive metal plates.

3. A measurement cell as recited in claim 1 further comprising;
first and second housing members, the interleaved sets of plates being attached to, but electrically insulated from, the first housing member, and
one of the housing members having an opening for admission of liquid to and between the interleaved sets of plates.

4. A measurement cell as recited in claim 1 further comprising:
first and second housing members, the interleaved sets of plates being attached to the first housing member with electrically non-conductive fasteners, and the interleaved sets of plates being insulated from the first housing member;
and one of the housing members having an opening for admission of liquid to and between the interleaved sets of plates and an opening for electrical leads to the first and second electrical connections.

5. A measurement cell as recited in claim 1 in which the interleaved plates of the first and second sets are of the same circular or regular polygonal peripheral shape and size, and each pair of facing plates presents faces having the same surface area for electrical conduction through an intervening liquid.

6. A measurement cell as recited in claim 5 in which plates of the first set have equally spaced holes at their periphery for electrical connections to other members of the first set of plates, and the plates of the second set have equally spaced holes at their periphery for electrical connections to other members of the second set of plates.

7. A measurement cell as recited in claim 3 in which the interleaved plates are attached to the first housing member with non-conductive, non-metallic bolts.

8. A measurement cell as recited in claim 1 in which the thickness of each metal plate is in the range of about 0.1 mm to about 3 mm.

9. A measurement cell for determining the resistivity and/or permittivity of a liquid, the cell comprising:
a first and second set of electrically conductive metal plates with each plate having opposing plate faces, the first set of plates being interleaved in parallel and equally spaced facing relationship with the plate faces of the second set of electrically conductive metal plates, the number of plates respectively in said first set and second set, the dimensions of the plates, and the spacing between the alternating plates of the first and second sets being predetermined for the liquid to be placed or flowed between them for determination of the present value of the liquid's resistivity and/or permittivity;
a first set of tubular electrically conductive metal connectors electrically connecting pairs of plates of the first set, the first set of tubular connectors having an external insulation layer for electrical insulation from interposed plates of the second set of plates;
a second set of tubular electrically conductive metal connectors electrically connecting pairs of plates of the second set, the second set of tubular connectors having an external insulation layer for electrical insulation from interposed plates of the first set of plates; and
a first electrical connection to one plate of the first set of plates and a second electrical connection to one plate of the second set of plates for delivery of variable and high frequency electrical signals to the plates; the insulation layers on the tubular connectors between facing plates promoting current flow through an intervening liquid perpendicularly to the faces of each pair of facing plates.

10. A measurement cell as recited in claim 9 in which the first set of electrically conductive metal plates has one more plate than the second set of electrically conductive metal plates.

11. A measurement cell as recited in claim 9 in which plates of the first set have equally spaced holes at their periphery for the second set of external insulation layer bearing tubular connectors, and the plates of the second set have equally spaced holes at their periphery for the first set of external insulation layer bearing tubular connectors, and the interleaved plates are attached to a first housing member with non-conductive bolts.

12. A measurement cell as recited in claim 9 in which the thickness of each metal plate is in the range of about 0.1 mm to about 3 mm.

* * * * *